US006258552B1

(12) United States Patent
Shiraki et al.

(10) Patent No.: US 6,258,552 B1
(45) Date of Patent: Jul. 10, 2001

(54) ESTIMATION OF CHANGE IN BONE MINERAL DENSITY AND DIAGNOSIS OF OSTEOPOROSIS

(75) Inventors: Masataka Shiraki, Minamiazumi-gun; Jui-Tung Chen, Minato-ku; Ikuo Morita, Itabashi-ku; Naoko Maruo, Yokohama, all of (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 08/603,121

(22) Filed: Feb. 20, 1996

(30) Foreign Application Priority Data

Feb. 23, 1995 (JP) .................................................... 7-035349

(51) Int. Cl.$^7$ .......................... G01N 33/53; G01N 21/76; C07K 16/00
(52) U.S. Cl. .......................... 435/7.94; 435/334; 436/527; 436/172; 530/388.22; 530/389.2; 530/391.1; 530/391.3
(58) Field of Search ................................... 435/7.2, 7.92, 435/7.94, 69.1, 69.52, 328, 334, 335; 530/350, 300, 395, 388.22, 389.2, 391.1, 391.3; 436/518, 524, 527, 63, 172

(56) References Cited

U.S. PATENT DOCUMENTS

| 4,959,302 | 9/1990 | Cornaby et al. ........................ 435/5 |
| 5,132,403 | 7/1992 | Kishimoto ............................ 530/351 |
| 5,171,840 | 12/1992 | Kishimoto ............................ 530/350 |
| 5,223,611 | 6/1993 | Kishimoto ............................ 530/351 |
| 5,480,796 | 1/1996 | Kishimoto ....................... 435/240.27 |

FOREIGN PATENT DOCUMENTS

| 0 409 607 | 1/1991 | (EP) . |
| 0 429 607 | 1/1991 | (EP) . |
| 3-139293 | 6/1991 | (JP) . |
| 3-155795 | 7/1991 | (JP) . |
| 4-99800 | 3/1992 | (JP) . |

OTHER PUBLICATIONS

Honda et al, The Journal of Immunology, vol. 148, pp. 2175–2180, No. 7, Apr. 1992.*
Manolagas et al, Int. J. Immunopharmac., vol. 17. No. 2, pp. 109–116, 1995.*
Ralston, Stuart H., Chemical Abstracts, vol. 123, No. 9, Aug. 28, 1995, No. 103618v.
J. Biochem., 108, 1992, pp. 673–676., Yasukawa et al.
Tamura et al., Proc. Natl. Acad. Sci., USA 90, 1993, pp. 11924–11928.

\* cited by examiner

*Primary Examiner*—Keith MacMillan
*Assistant Examiner*—P. Ponnalun
(74) *Attorney, Agent, or Firm*—Jacobson, Price, Holman & Stern, PLLC

(57) ABSTRACT

A method for estimation of change in bone mineral density or a method for diagnosis of osteoporosis, comprising the step of measuring change in a concentration of soluble interleukin-6 receptor in a blood sample, by for example, sandwich assay or competition assay; and a kit for carrying out the methods, comprising:

(1) an anti-sIL-6R antibody immobilized to a solid carrier, and
(2) an anti-sIL-6R antibody bound to a detectable marker or capable of binding to a detectable marker.

44 Claims, 2 Drawing Sheets

ESTIMATION OF CHANGE IN BONE MINERAL DENSITY AND DIAGNOSIS OF OSTEOPOROSIS

BACKGROUND OF INVENTION

1. Field of Invention

The present invention relates a method for estimation of change in bone mineral density and a method for diagnosis of osteoporosis as well as a kit used for said methods.

2. Related Art

Interleukin-6 (IL-6) is reported to be a multifunctional cytokine, and it has recently become known that one of the functions of IL-6 is stimulation of bone absorption. On the other hand, it is also known that a decrease in the secretion of estradiol in the post-menopausal phase results in an increase of the production of IL-6, and on the basis of these findings, it has been pointed out that there is a possibility that IL-6 is involved in causing osteoporosis.

Interleukin-6 receptor (IL-6R) is a protein which has a molecular weight of about 80 kDa and binds with IL-6 resulting in formation of a ligand-receptor complex. The complex of IL-6 and IL-6R, in turn, binds with a protein called gp130 protein, having a molecular weight of about 130 kDa, so as to be responsible for IL-6-mediated signal transduction (Japanese Unexamined Patent Publication (Kokai) No. 4-29997).

IL-6R is a membrane protein comprising a intramembrane domain, a membrane-penetrating portion and an extracellular domain, and it is known that the extracellular domain having a molecular weight of about 55 kDa is detected in serum and urine (Eur. J. Immunol. Vol. 23, pp. 820–824, 1993).

It is reported that soluble IL-6R (sIL-6R), which is a part of IL-6R and is detected in serum and urine, increases in a patient with myeloma or AIDS, and therefore it is considered that the sIL-6R plays an important role in IL-6R-related diseases (Guilard J. P. et al., Eur. J. Immunol. Vol. 23, pp 820–824, 1993; and Honda M. et al., J. Immunol. Vol. 148, pp. 2175–2180, 1992).

With coming of the so-called high-age society, the number of patients suffering from osteoporosis is increasing, and the foreseeing and treatment thereof are becoming an important matter. One of the most important things relating to osteoporosis is to determined the risk of osteoporosis as easily as possible and to prevent the occurance thereof.

A factor most directly related to the frequency of generation of bone fractures is the amount of bone (bone mineral density), and the bone mineral density is measured by image diagnosis and X-ray absorption methods. Among them, at present, dual X-ray absorptiometry (DXA) is the most popular method, and its reliability is high. However, the apparatus for DXA is so expensive that only a few hospitals have the apparatus, and thus the DXA is difficult to use routinely. Morover, since DXA uses radiation, this method cannot be applied to pregnant women. In addition, although the DXA method can be used to measure bone mineral density at the point time in at which the measurement is carried out, it cannot be used to estimate a future decrease of bone mineral density, in other words, DXA cannot show metabolic turnover of bone.

On the other hand, it is considered that post-menopausal osteoporosis is caused by an unbalance between bone formation and bone resorption resulting in an increase of bone resorption, and measurement of a bone metabolism marker which reflects bone metabolism is brought to attention.

Although as a biochemical marker of bone metabolism which can be used to selectively evaluate bone resorption, deoxypyridinoline is brought to attention; and as marker of bone metabolism which can be used to evaluate bone formation osteocalcin is brought to attention, the former is disadvantageous in that since it is measured in a urine sample, the results vary during a day, and are influenced by kidney clearance functions. The obtained data should be corrected using creatinaine concentration. On the other hand, the latter is disadvantageous in that a sample serum includes various degradation products of osteocalcin, and the component measured is not clear.

As can be seen from the above, although the importance of the estimation and diagnosis of the osteoporosis has been recognized, at present, there is no routine method for measurement of a bone metabolism marker.

SUMMARY OF INVENTION

The present inventors, in the above-mentioned state of the art, searched for substances whose concentration changes concomitantly with the loss or increase of bone mineral density which causes the osteoporosis, and as a result found that the concentration of sIL-6R in a blood sample increases with a loss of bone mineral density, and completed the present invention.

Accordingly, the present invention provides a method for estimation of change in bone mineral density, comprising the step of measuring change in a concentration of soluble interleukin-6 receptor (sIL-6R) in a blood sample.

The present invention further provides a method for diagnosis of osteoporosis comprising the step of measuring the concentration of sIL-6R in a blood sample.

The present invention still further provides a kit for estimating change in bone mineral density or diagnosis of osteoporosis, comprising:

(1) an anti-sIL-6R antibody immobilized to a solid carrier, and (2) an anti-sIL-6R antibody which is bound to a detectable marker or which can bind to a detectable marker.

DETAILED DESCRIPTION OF INVENTION

Figure 1:
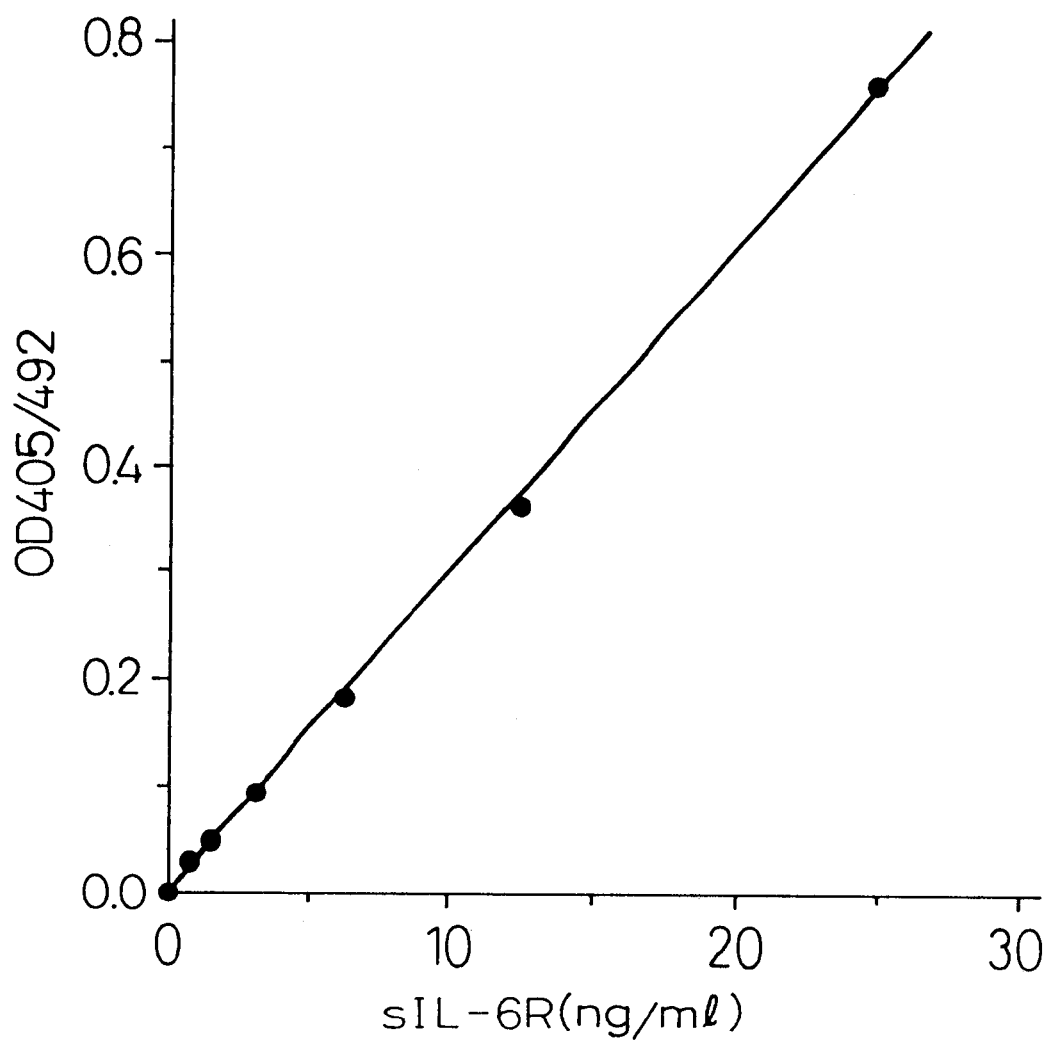
FIG. 1 represents a standard curve for a sandwich assay system for IL-6R established in Example 1, wherein the vertical axis shows the absorbance, and the horizontal axis shows IL-6R concentration (ng/ml). This figure shows that the sandwich assay system can measure IL-6R in the range of concentration of 0.39 to 25 mg/ml. The line is represented by the equation $Y=2.9577 \times 10^{-2} X - 4.0200 \times 10^{-5}$, wherein Y represents the absorbance and X represents the sIL-6R concentration.

The present invention relates to a method for estimation of change in bone mineral density and method for diagnosis of osteoporosis, comprising the steps of measuring a concentration of sIL-6R in a blood sample. Since it is known that IL-6 and IL-6R are present in mammals other than humans (for example, see for mouse, Japanese Unexamined Patent Publication (Kokai) No. 3-155795), the present invention can be applied to estimate change in bone mineral density in mammals other than humans. However, the present invention is preferably applied to estimate the change in bone mineral density or diagnosis of osteoporosis in human.

According to the present invention, the sIL-6R refers to any IL-6R fragment comprising a functional domain which exhibits the function of IL-6R, i.e., essential domain of signal transduction mediated by IL-6. More specifically, for human IL-6R, the functional domain is present in the region of the 123rd to 323rd amino acid residues calculating from the N terminal amino acid of human IL-6R comprising 468 amino acids. Therefore, the sIL-6R includes those IL-6R fragments which comprise at least said functional domain, are liberated from the cell membrane and have various different molecular weights (for example, see, U.S. Pat. No. 5,171,840). A representative sIL-6R is the above-mentioned IL-6R fragment having a molecular weight of about 55 kDa.

The blood sample of the present invention is any blood sample used in an immunoassay, and is typically a serum sample. To estimate the change in bone mineral density or to diagnose osteoporosis in humans, a human blood sample, preferably a human serum sample is used.

According to the present invention, sIL-6R may be measured by any conventional immunoassay such as sandwich assay or competitive assay. For example in the case of sandwich assay, an anti-sIL-6R antibody immobilized in a solid carrier, and an anti sIL-6R antibody bound to a detectable marker or capable of binding to a detectable marker are used. In addition, for example, in the case of competitive assay, an anti sIL-6R antibody immobilized on a solid carrier, and an sIL-6R bound to a detectable marker or capable of binding to a detectable marker are used.

In the sandwich assay, an anti-IL-6R antibody is immobilized on the surface of a solid carrier. The solid carrier may be a microtiter plate, beads, etc. The anti-IL-6R antibody is immobilized on the surface of a solid carrier by a conventional procedure, for example, bringing a solid carrier in contact with an aqueous solution of an anti-IL-6R antibody and incubating the solid carrier and the solution, for example, at room temperature for 1–24 hours, and preferably 12 to 16 hours. The aqueous solution is preferably a buffer solution such as phosphate buffer, Tris-HCl or carbonate buffer at pH 6 to 10.

Next, a sample is brought in contact with the solid carrier coated with an anti-IL-6R antibody as the first antibody, and the whole is incubated, for example at room temperature for 10 to 240 minutes, preferably 60 to 120 minutes. In this way, sIL-6R in the sample, if any, binds to the anti-IL-6R antibody immobilized on the solid state, so that the sIL-6R in the sample is immobilized on the solid carrier via the anti-IL-6R antibody previously immobilized on the solid carrier. Next, another anti-IL-6R antibody (second antibody) bound to a marker is added to the solid carrier so as to allow the anti-IL-6R antibody labeled with the marker binding to the sIL-6R which has been immobilized on the solid carrier.

Alternatively, a sample and an anti-IL-6R antibody bound to a marker are mixed so that sIL-6R, if any, in the sample immunologically binds with the anti-IL-6R antibody (second antibody) to form an immunocomplex and then the mixture is brought into contact with the anti-IL-6R antibody (first antibody) previously immobilized in the solid carrier so that the sIL-6R in the immunocomplex binds to the anti-IL-6R antibody immobilized on the solid carrier. In this way the marker is immobilized in an amount which reflects an amount of sIL-6R in the sample. The anti-IL-6R antibody as the first antibody and the anti IL-6R antibody as the second antibody should bind to different epitopes on the sIL-6R molecule. Both the first and second antibody are polyclonal antibodies or monoclonal antibodies. Alternatively the first antibody is a monoclonal antibody and the second antibody is polyclonal antibody; or the first antibody is a polyclonal antibody and the second antibody is a monoclonal antibody.

In the competitive assay, an anti-IL-6R antibody as the first antibody is immobilized on the surface of a solid carrier as described for the sandwich assay. The solid carrier for the competitive assay may be same as those for the sandwich assay. Next, a sample and sIL-6R bound to a marker is mixed and the mixture is brought into contact with the solid carrier coated with the anti-IL-6R antibody, so as to allow competition between sIL-6R, if any, in the sample and the sIL-6R bound to the marker to the anti-IL-6R antibody immobilized on the solid carrier. In this way, the marker is immobilized on the surface of the solid carrier in an amount which inversely reflects an amount of sIL-6R in the sample.

In addition to the above-mentioned sandwich assay and competitive assay, according to the present invention, estimation of change in density and diagnosis of osteoporosis can be carried out using a physical property of IL-6R. Namely, apart from the anti-sIL-6R antibodies, the IL-6R specifically binds to IL-6, and a complex of IL-6R and IL-6 specifically binds to gp130 protein. Therefore, for example, in the above-mentioned sandwich assay and competitive assay, the anti-sIL-6R antibody can be replaced with IL-6. More specifically, in the sandwich assay, one of the first and second antibodies can be replaced with IL-6. On the other hand, in the competitive assay, the anti-sIL-6 antibody to be immobilized on the solid carrier can be replaced with IL-6.

According to the present invention, although any of the above-mentioned methods can be used for sIL-6R assay, the sandwich assay is most preferable due to ease of preparation of assay reagents such as anti-sIL-6R antibody and high sensitivity.

The sIL-6R used in the present methods can be prepared, for example, according to the process described in U.S. Pat. No. 5,171,840. In addition, the sIL-6R thus prepared can be used as an antigen to prepare anti-sIL-6R antibodies, for example, as described in Japanese Unexamined Patent Publication (Kokai) No. 4-99800.

The marker used in the present methods may be any conventional marker used in immunoassay, and for example is a fluorescent substance, radioisotope, light-absorbing substance or enzyme. Among them enzymes are most preferable because of ease of handling without a special apparatus, and high sensitivity. The typical enzyme is alkaline phosphatase. The amount of alkaline phosphatase immobilized on the solid carrier dependent on the amount of sIL-6R in the sample is measured by a chromogenic substrate for the enzyme, such as p-nitrophenylphosphate, and an amount of released p-nitrophenol is spectrophotometrically measured, for example, by a commercially available plate reader.

As shown in detail in the examples, a change (increase) of concentration of sIL-6R in a blood sample correlates with a change (decrease) of bone mineral density. Therefore, according to the present invention, changes in bone mineral density can be estimated by observing changes in concentration of sIL-6R. Especially, changes in bone mineral density of a particular patient can be monitored by periodically measuring sIL-6R in samples obtained from the same patient. In addition, if a concentration of sIL-6R in a blood sample from a patient exceeds a predetermined level, the patient may be diagnosed as having osteoporosis.

EXAMPLES

Next, the present invention is explained in more definitely by Examples, although the scope of the invention is not limited thereto.

Example 1
Establishment of assay method for sIL-6R

An anti-IL-6R monoclonal antibody PM1 (see, Japanese Unexamined Patent Publication (Kokai) No. 3-139293) capable of binding to sIL-6R was dissolved in 0.1M carbonate buffer (pH 9.6) to final concentration of 5 µg/ml, and 100 µl/well of the solution was added to each well of a 96-well plate (solid carrier), and the whole was incubated at 4° C. overnight to allow the antibody immobilizing on the wells of the plate. The plate was washed with PBS (phosphate-buffered saline) containing 0.02% Tween 20. 150 µl/well of PBS containing 0.5% BSA was added to the wells, and the plate was allowed to stand at 4° C. overnight, for blocking.

Anti-IL-6R monoclonal antibody labeled with alkaline phosphatase (ALP) was prepared as follows: 2 mg of anti-IL-6R monoclonal antibody MT18 (see Japanese Unexamined Patent Publication (Kokai) No. 2-288898) and 2 mg of a commercially available alkaline phosphatase of calf small intestine were linked via S—S bonds, and the product was purified by subjecting the reaction mixture to gel filtration (column: G3000S W, Tosoh; elution buffer: 50 mM phosphate buffer (pH 7) containing 150 mM NaCl) (see, Koso Meneki Sokutei Ho. third ed., ed by Eiji Ishikawa et al., Igaku Shoin, page 117).

To prepare standard IL-6R solutions, IL-6R prepared by a method of Yasukawa K. et al., J. Biochem. Vol. 108, pp. 673 –676, 1990 was dissolved with a dissolving solution (0.1M Tris-HCl (pH 8.0), 1 mM $MgCl_2$, 0.1 mM $ZnCl_2$, 1% BSA) to set the final concentration of the IL-6R to 25, 12.5, 6.25, 3.13, 1.56, 0.78 and 0.36 mg/ml.

The plate was washed with PBS containing 0.02% Tween 20, and 50 µl of the standard solution and 50 µl of a solution containing 1 mA of the ALP-labeled antibody (1 mA is a concentration of the ALP-labeled antibody which provides an absorption of at 280 mm 0.001) were added to each well, and the plate was allowed to stand at room temperature for 2 hours so that the standard sIL-6R and the ALP-labeled antibody bind. After washing the plate, 100 µl of a solution of 1 mg/ml p-nitrophosphate in 0.05M carbonate buffer (pH 9.8) was added to each well so as to allow the ALP-labeled antibody immobilized on the solid carrier reacting with the p-nitrophenylphosphate, and an amount of resulting p-nitrophenol was photospectrometrically measured using a commercially available plate reader (MPR-A4, Tosoh) at a wavelength of 405 nm, with a reference wavelength of 492 nm.

The result is shown in FIG. 1. As can be seen from FIG. 1, IL-6R can be measured in the range of 0.39 to 25 ng/ml.

Example 2
Measurement of sIL-6R in serum sample from women

Serum samples were obtained from healthy female outpatients, 44 to 65 years old, who visited gynecological hospital. The samples include 65 samples from pre-menopausal women, 35 samples from peri-menopausal women and 51 samples from post-menopausal women.

The serum samples obtained were stored at −80° C. until measurement. For assay of sIL-6R, the serum samples were diluted 60-fold with the dilution solution described in Example 1, and assay was carried out according to the same procedure as described in Example 1. Note that for comparison, concentration of IL-6 in the same samples was measured by sandwich assay using an anti-IL-6 antibody immobilized on a solid carrier and an anti-IL-6 antibody labeled with ALP.

Figure 2:
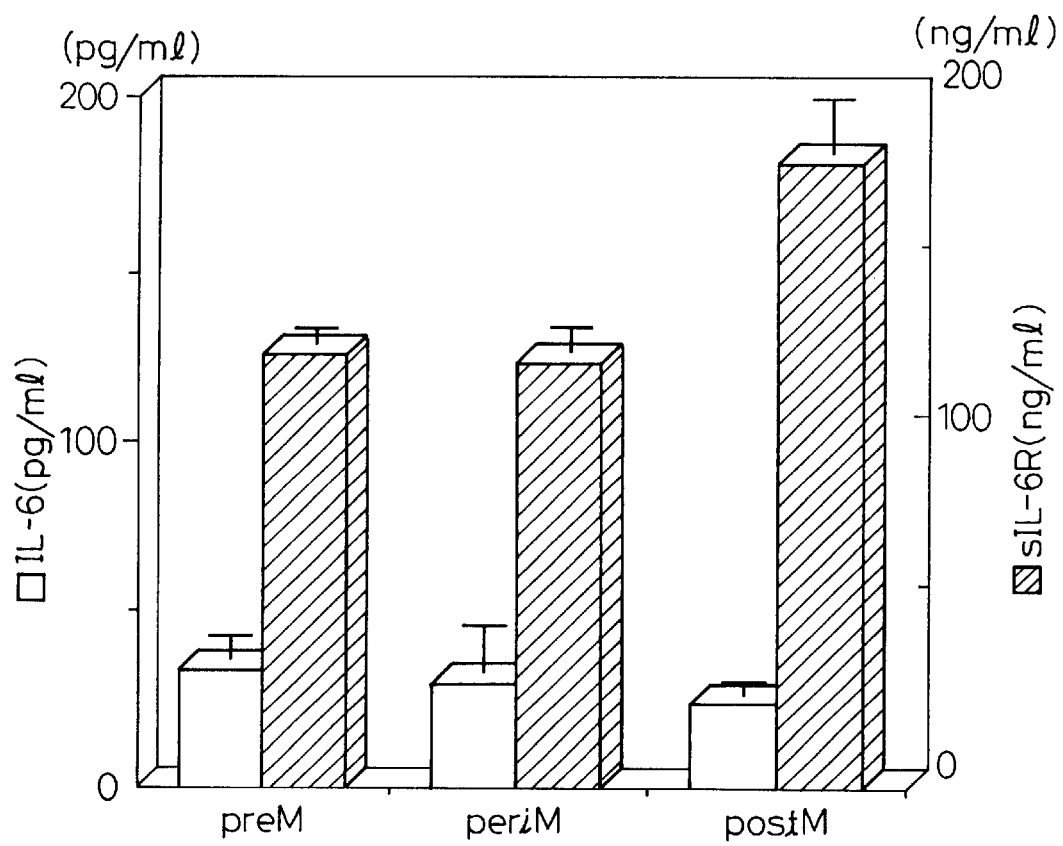
FIG. 2 represents a graph showing a result of measurements carried out in Example 2 of IL-6R and sIL-6R in serum samples from pre-menopausal, peri-menopausal and post-menopausal women, wherein the vertical axis shows the concentration of sIL-6R (ng/ml) or IL-6R (pg/ml), and the horizonal axis classifies the results of pre-menopausal (preM), peri-menoposal (periM) and post-menopausal (postM) samples. This figure shows that the concentration of sIL-6R (hatched bars) are significantly different in pre-menopausal women and post-menopausal women, while the concentrations of IL-6 (blanked bars) are not significantly different between pre-menopausal women and post-menopausal women.

FIG. 2 represents a graph showing concentrations of IL-6R and sIL-6R measured in sera from pre-menopausal, peri-menopausal and post-menopausal women. Concentrations (mean value±standard error) of sIL-6R in serum samples were 125.95±4.29 ng/ml, 122.81±7.40 ng/ml and 180.26±15.18 ng/ml respectively, revealing that the concentration of sIL-6R in serum samples from post-menopausal women is significantly higher than that in the other two groups. On the contrary, there is no significant difference in concentrations of IL-6 in serum samples obtained from pre-menopausal, peri-menopausal and post-menopausal women. Note that the statistical significance was determined according to the Mann-Whitney test (U test).

Example 3
Corelation between measured value of sIL-6R and DXA

Figure 3:
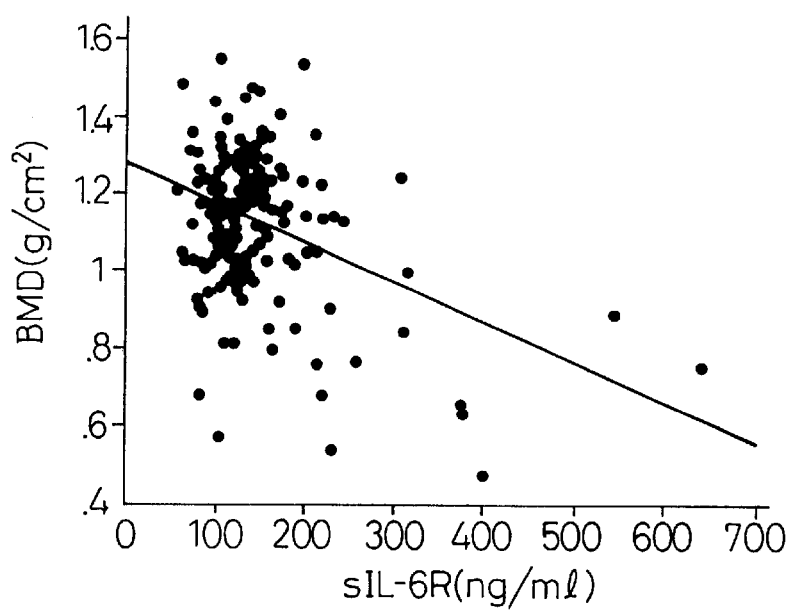
FIG. 3 shows the corelation between the concentration of sIL-6R measured according to the present invention and the bone mineral density measured by the conventional DXA method, wherein the vertical axis shows bone mineral density (g/cm$^2$), and the horizontal axis shows concentration of sIL-6R (ng/ml). As can be seen from this figure, the concentration of sIL-6R is lower as the DXA value representing bone mineral density is higher, and the concentration of sIL-6R is higher as the DXA value representing bone mineral density is lower.

It has been reported that in post-menopausal women, bone mineral density decreases, and the decrease of the bone mineral density causes the osteoporosis. In this Example, bone mineral density of the lumbar bone of the 151 patients referred to Example 2 was measured by a Lunar DPX-L (Lunar Inc.), and the correlation between value of sIL-6R measured by the present method and DXA value was observed. The result is shown in FIG. 3. As can be seen from FIG. 3, the value of sIL-6R was higher, as the bone mineral density was lower, and the coefficient of correlation was 0.4.

Example 4
Relationship between measured value of sIL-6R and serum osteocalcin or urine deoxypvridinoline value For the 151 patients referred to in Example 2, serum osteocalcin value (intact osteocalcin conc.-N-terminal osteocalcin conc.) and urine deoxypyridinoline value (corrected using creatinine concentration) which are known as an indication of bone metabolism were measured and compared with value of sIL-6R measured by the present method.

Table 1 shows the correlation coefficient between bone mineral density and sIL-6R, serum osteocalcin value or urine deoxypyridioline (creatinine-corrected). Table 1 shows that sIL-6R has the highest relationship with bone mineral density among conventional biochemical members of bone metabolism. Note that there is also a correlation between serum sIL-6R and serum osteocalcin value or creatinine-corrected urine deoxypyridinoline value, and an increase in sIL-6R value reflects the bone metabolism.

TABLE 1

| | Correlation coefficient |
|---|---|
| Serum sIL-6R | 0.400 |
| Serum osteocalcin | 0.327 |
| Urine deoxypyridinoline (creatine-corrected) | 0.375 |

According to the present invention, by using a blood sample such as a serum sample which is relatively easily taken, estimation of changes in bone mineral density and diagnosis of osteoporosis are possible. The present methods can be routinely carried out according to conventional immunoassay without using a special apparatus. In addition, according to the present methods, applying radiation to the human body is not necessary, and therefore the present method is safe.

As is clear from the above explanation, as concentration of sIL-6R in a blood sample increases, bone mineral density decreases. Accordingly, by observing the change of a concentration of sIL-6R by the present invention, the change of bone mineral density can be monitored, and in addition, when a concentration of sIL-6R in a blood sample is over a predetermined level, the osteoporosis can be diagnosed.

What is claimed is:

1. A method for estimation of change in bone mineral density, comprising the steps of:
   (1) bringing a blood sample into contact with a solid carrier on the surface of which an anti soluble interleukin-6 receptor (sIL-6R) antibody (first antibody) has been immobilized;
   (2) bringing into contact with the solid carrier from the step (1)
      (i) an anti sIL-6R antibody (second antibody) bound to a detectable marker, or
      (ii) an anti sIL-6R antibody (second antibody) capable of binding to a detectable marker, followed by bringing a detectable marker into contact with the anti sIL-6R antibody (second antibody); and
   (3) measuring the amount of the detectable marker immobilized on the solid carrier, wherein the amount of the immobilized detectable marker relates to an amount of sIL-6R in the blood sample, and the amount of sIL-6R relates to the bone mineral density.

2. A method according to claim 1 wherein the blood sample is a serum sample.

3. A method according to claim 1, wherein the blood sample is of a human, and the sIL-6R is a human sIL-6R.

4. A method according to claim 1, wherein the first and second antibodies are monoclonal antibodies or polyclonal antibodies.

5. A method according to claim 1, wherein each of the first and second antibodies is independently a monoclonal antibody or a polyclonal antibody.

6. A method for estimation of change in bone mineral density, comprising the steps of:
   (1) contacting a blood sample with anti sIL-6R antibody (second antibody) bound to a detectable marker, thereby forming a mixture;
   (2) bringing the mixture from the step (1) into contact with a solid carrier on the surface of which an anti IL-6R antibody (first antibody) has been immobilized; and
   (3) measuring the amount of the detectable marker immobilized on the solid carrier, wherein the amount of the immobilized detectable marker relates to an amount of sIL-6R in the blood sample, and the amount of sIL-6R relates to the bone mineral density.

7. A method according to claim 6, wherein the blood sample is a serum sample.

8. A method according to claim 6, wherein the blood sample is of a human, and the sIL-6R is a human sIL-6R.

9. A method according to claim 6, wherein the first and second antibodies are monoclonal antibodies or polyclonal antibodies.

10. A method according to claim 6, wherein each of the first and second antibodies is independently a monoclonal antibody or a polyclonal antibody.

11. A kit for estimating change in bone mineral density or diagnosis of osteoporosis, comprising:
   (1) an anti-sIL-6R antibody immobilized to a solid carrier, and
   (2) an anti-sIL-6R antibody which is bound to a detectable marker or which is capable of binding a detectable marker.

12. A method for estimation of change in bone mineral density, comprising the steps of:
   (1) bringing a blood sample, an anti sIL-6R antibody (second antibody), and a detectable marker into contact with a solid carrier on the surface of which an anti sIL-6R antibody (first antibody) has been immobilized, wherein the anti sIL-5R antibody and the detectable marker are optionally bound together before mixing; and
   (2) measuring the amount of the detectable marker immobilized on the solid carrier, wherein the amount of the immobilized detectable carrier relates to an amount of sIL-6R in the blood sample, and the amount of sIL-6R in the blood sample relates to the bone mineral density.

13. A method according to claim 12, wherein the blood sample is a serum sample.

14. A method according to claim 12, wherein the blood sample is a human blood sample, and the sIL-6R is a human sIL-6R.

15. A method according to claim 12, wherein the first and second antibodies are monoclonal antibodies or polyclonal antibodies.

16. A method according to claim 12, wherein each of the first and second antibodies is independently a monoclonal antibody or a polyclonal antibody.

17. A method according to claim 12, for diagnosis of osteoporosis.

18. A method for estimation of change in bone mineral density, comprising the steps of:
   (1) contacting a blood sample with a marker-bound sIL-6R, thereby forming a mixture;
   (2) bringing the mixture into contact with a solid carrier on the surface of which an anti sIL-6R antibody has been immobilized; and
   (3) measuring the amount of the marker immobilized on the solid carrier, wherein the amount of the immobilized marker reversely reflects an amount of sIL-6R in the sample, and the amount of sIL-6R relates to the bone mineral density.

19. A method according to claim 18, wherein the blood sample is a serum sample.

20. A method according to claim 18, wherein the blood sample is a human blood sample, and the sIL-6R is a human sIL-6R.

21. A method according to claim 18, wherein the antibody is a monoclonal antibody or polyclonal antibody.

22. A method for diagnosis of osteoporosis, comprising the steps of:
(1) bringing a blood sample into contact with a solid carrier on the surface of which an anti sIL-6R antibody (first antibody) has been immobilized;
(2) bringing into contact with the solid carrier from the step (1)
   (i) an anti sIL-6R antibody (second antibody) bound to a detectable marker, or
   (ii) an anti sIL-6R antibody (second antibody) capable of binding to a detectable marker, followed by bringing a detectable marker into contact with the anti sIL-6R antibody (second antibody); and
(3) measuring the amount of the detectable marker immobilized on the solid carrier, wherein the amount of the immobilized detectable carrier relates to an amount of sIL-6R in the blood sample, and the amount of sIL-6R relates to the diagnosis of the osteoporosis.

23. A method according to claim 22, wherein the blood sample is a serum sample.

24. A method according to claim 22, wherein the blood sample is a human blood sample, and the sIL-6R is a human sIL-6R.

25. A method according to claim 22, wherein the first and second antibodies are monoclonal antibodies or polyclonal antibodies.

26. A method according to claim 22, wherein each of the first and second antibodies is independently a monoclonal antibody or a polyclonal antibody.

27. A method according to claim 22, wherein the osteoporosis is post-menopausal osteoporosis.

28. A method for diagnosis of osteoporosis, comprising the steps of:
(1) contacting a blood sample suspected to contain sIL-6R and an anti sIL-6R antibody (second antibody) bound to a detectable marker, thereby forming a mixture;
(2) bringing the mixture from the step (1) into contact with a solid carrier on the surface of which an anti IL-6R antibody (first antibody) has been immobilized; and
(3) measuring the amount of the detectable marker immobilized on the solid carrier, wherein the amount of the immobilized detectable marker relates to an amount of sIL-6R in the blood sample, and the amount of sIL-6R relates to the diagnosis of the osteoporosis.

29. A method according to claim 28, wherein the blood sample is a serum sample.

30. A method according to claim 28, wherein the blood sample is a human blood sample, and the sIL-6R is a human sIL-6R.

31. A method according to claim 28, wherein the first and second antibodies are monoclonal antibodies or polyclonal antibodies.

32. A method according to claim 28, wherein each of the first and second antibodies is independently a monoclonal antibody or a polyclonal antibody.

33. A method according to claim 28, wherein the osteoporosis is post-menopausal osteoporosis.

34. A method for diagnosis of osteoporosis, comprising the steps of:
(1) bringing a blood sample, an anti sIL-6R antibody (second antibody), and a detectable marker into contact with a solid carrier on the surface of which an anti sIL-6R antibody (first antibody) has been immobilized, wherein the anti sIL-6R antibody and the detectable marker are optionally bound together before mixing; and
(2) measuring the amount of the detectable marker immobilized on the solid carrier, wherein the amount of the immobilized detectable carrier relates to an amount of sIL-6R in the blood sample, and the amount of sIL-6R relates to the diagnosis of the osteoporosis.

35. A method according to claim 34, wherein the blood sample is a serum sample.

36. A method according to claim 34, wherein the blood sample is a human blood sample, and the sIL-6R is a human sIL-6R.

37. A method according to claim 34, wherein the first and second antibodies are monoclonal antibodies or polyclonal antibodies.

38. A method according to claim 34, wherein each of the first and second antibodies is independently a monoclonal antibody or a polyclonal antibody.

39. A method according to claim 34, wherein the osteoporosis is post-menopausal osteoporosis.

40. A method for diagnosis of osteoporosis, comprising the steps of:
(1) contacting a blood sample and a marker-bound sIL-6R, thereby forming a mixture;
(2) bringing the mixture into contact with a solid carrier on the surface of which an anti IL-6R antibody has been immobilized; and
(3) measuring the amount of the marker immobilized on the solid carrier, wherein the amount of the immobilized marker reversely reflects an amount of sIL-6R in the sample, and the amount of sIL-6R relates to the diagnosis of osteoporosis.

41. A method according to claim 40, wherein the blood sample is a serum sample.

42. A method according to claim 40, wherein the blood sample is a human blood sample, and the sIL-6R is a human sIL-6R.

43. A method according to claim 40, wherein the antibody is a monoclonal antibody or polyclonal antibody.

44. A method according to claim 40, wherein the osteoporosis is post-menopausal osteoporosis.

* * * * *